(12) United States Patent
Ben Haim

(10) Patent No.: US 8,986,610 B2
(45) Date of Patent: Mar. 24, 2015

(54) APPARATUS AND METHOD FOR DISPERSING LIQUID IN AEROSOL

(71) Applicant: Roei Ben Haim, Aventura, FL (US)

(72) Inventor: Roei Ben Haim, Aventura, FL (US)

(*) Notice: Subject to any disclaimer, the term of this patent is extended or adjusted under 35 U.S.C. 154(b) by 0 days.

(21) Appl. No.: 14/160,330

(22) Filed: Jan. 21, 2014

(65) Prior Publication Data

US 2014/0203100 A1     Jul. 24, 2014

Related U.S. Application Data

(60) Provisional application No. 61/755,129, filed on Jan. 22, 2013.

(51) Int. Cl.
| | |
|---|---|
| *A62B 7/08* | (2006.01) |
| *A61L 9/00* | (2006.01) |
| *B01D 47/00* | (2006.01) |
| *A61L 9/04* | (2006.01) |
| *A24F 25/00* | (2006.01) |
| *A61M 11/02* | (2006.01) |

(52) U.S. Cl.
CPC .................................. *A61M 11/02* (2013.01)
USPC ............ 422/28; 422/123; 422/305; 422/306; 261/2; 261/76; 261/78.2; 239/6; 239/34; 239/8; 239/337; 239/418

(58) Field of Classification Search
CPC .............. A61L 2/00; A61L 2/22; A61L 9/00; A61L 9/14; A61M 11/00
USPC .............. 422/1, 28, 123, 305–306; 261/2, 76, 261/78.2; 239/6, 34, 8, 337, 418; 96/4; 128/200.14
See application file for complete search history.

(56) References Cited

U.S. PATENT DOCUMENTS

2009/0238716 A1*   9/2009   Weening .......................... 422/3

* cited by examiner

*Primary Examiner* — Monzer R Chorbaji
(74) *Attorney, Agent, or Firm* — David W. Barman

(57) ABSTRACT

A system and method delivers an atomized solution to the interior volume of a building or room utilizing a venturi effect for the atomization.

14 Claims, 22 Drawing Sheets

Table 1 (Before)

Concentration of Fungal counts in units of $CT/cm^{2}$ in filter n⁰ 1 of the AHU

| # | Sample Location | Cladosporium | Penicillium |
|---|---|---|---|
| 1 | Center of Filter | 84,000 | 38,000 |
| 2 | Top Left of Filter | 6 | 4,200 |
| 3 | Bottom Right of Filter | 2 | 2,400 |

FIG 16

Table 1 (After)

Concentration of Fungal counts in unites of count/cm$^2$* in filter n$^\circ$ 1 of the AHU

| # | Sample Location | Cladosporium |
|---|---|---|
| 1 | Center of Filter | NFD** |
| 2 | Top Left of Filter | NFD** |
| 3 | Bottom Right of Filter | 100 |

FIG 18

Table 2 (Before)

Concentration of Fungal counts in units of CT/cm$^2$ in filter n° 2 of the AHU

| # | Sample Location | Alternaria | Aspergilus | Cladosporium |
|---|---|---|---|---|
| 1 | Center of Filter | 2,000 | 78,000 | 40,000 |
| 2 | Top Left of Filter | N/A | N/A | N/A |
| 3 | Bottom Right of Filter | N/A | N/A | N/A |

FIG 20

Observation: During the experiment, fluctuation in level of certain Fungi occurred in filter n° 1 of the AHU i.e:

- After 24h of application, 300 – 1600 Penicillium
- After 48h of application, NFD
- After 72h of application, NFD \* CT/cm² – Counts per Square Meter \*\* NFD – No Fungi Detected Table 2 (After)

Concentration of Fungal counts in unites of count/cm$^{2*}$ in filter n$^\circ$ 2 of the AHU

| # | Sample Location | Results |
|---|---|---|
| 1 | Center of Filter | NFD** |
| 2 | Top Left of Filter | NFD** |
| 3 | Bottom Right of Filter | NFD** |

FIG 22

APPARATUS AND METHOD FOR DISPERSING LIQUID IN AEROSOL

INDEX TO RELATED APPLICATIONS

This application is a non-provisional of, and claims benefit to U.S. Provisional Patent Application Ser. No. 61/755,129 filed Jan. 22, 2013 the disclosure of which is incorporated herein by reference in its entirety.

BACKGROUND OF THE INVENTION

Field of the Invention

There are numerous devices known to atomize a liquid and deliver into the surrounding air. Devices such as other vaporizers provide introducing to air various types of solutions in order to vaporize the solution and introduce it into the air in a room or habitable structure. Most of these devices focus on scenting, purifying, or humidifying air.

Other devices require a timer or are manually to be turned on or off with a switch.

There is a recognized need for a device configured to automatically atomize and deliver a solution to a specific volume of enclosed space while accounting for concentration of a delivered solution in a functional relationship based on the interior volume.

SUMMARY OF THE INVENTION

The present invention relates to an air-aerosol dispersing apparatus, which can work on its own as well as in conjunction with an HVAC system.

In one embodiment, the present invention relates to a preselected solution mixed with pro-biotic bacteria that is released into the air. The release is by the atomization of a solution mixed with pro-biotic bacteria that can be added to the air via the HVAC system, directly into a room, or combinations thereof. Prior devices are deficient in they all lack the quantitative measurement and usage of a functional amount of pro-biotic bacteria.

In one embodiment, the present invention has an at least one airflow sensor configured to eliminate user input. The airflow sensor will activate the device, as it will sense airflows as a result of the operation of an HVAC system.

In one embodiment, the present invention includes a microcomputer interface for programming the intervals and length of time the device will turn on each time. This enables the present invention the ability to perform independently from the HVAC system as desired.

In one embodiment, the present invention is a system and method configured for delivery of a measured and effective amount of a biologically functional solution into the air, HVAC system, or combinations thereof. In one embodiment, a pro-biotic bacteria solution is atomized light enough and carried by the airflow and pressure differential in HVAC systems.

In one embodiment, the mist itself is a Stabiotic®, which is a blend of pro-biotic *bacillus* strains of bacteria that have been stabilized and are also in spore form. Once the Probiotic is exposed to the mixture of water and/or air it becomes active. Upon contact with any particles in the air or on any surface, they immediately consume sustenance, allergens and other contaminants, thereby cleaning to the microscopic level and further deconstructing biofilm; thus providing an extremely effective way of cleaning and thus reducing the risk of infection.

In one embodiment, the adaptive device is configured for positioning on the ground, inside HVAC systems, on counter tops, or mounted on the wall. The device has interchangeable solutions so that the user can change and refill the removable bottle. The device will perform without the user having to interact with the apparatus on regular basis and does not require it to be switched on or off, allowing for a more automated operation.

In a preferred embodiment, the present invention is configured to incorporate delivery with a solution container engineered to receive compressed air and directing the air in the container to impart a venturi effect into a closed chemical container that contains the delivery solution. By pressing the air under pressure into the delivery solution chamber, the solution is atomized and directed outward through a configured outlet. The atomized solution air is directed into an exit hose to the outside environment.

To the accomplishment of the above, the invention is illustrated in the accompanying drawings. Attention is called to the fact, however, that the drawings are illustrative only. Variations are contemplated as being part of the invention, limited only by the scope of the claims.

It is an object of the present invention to have a system and method for atomizing a solution with at least one active component and delivering the atomized solution to an interior area of a structure in direct delivery to the interior atmosphere, delivery through a HVAC system, or combinations thereof.

In one embodiment the active component is a Probiotic, pharmaceutical medicament, or nutritional supplement.

In one embodiment, the atomized solution particles have a d90 average particle size distribution based on normal Gaussian curve at about 1.1 to 10 microns.

It is an object of the present invention to have a system and method for atomizing a solution with at least one active component and delivering the atomized solution to an interior area of a structure utilizing at least one sensor operatively associated with the atomization mechanism whereby the sensor actuated atomization.

Additional features include configurations with control abilities via RF or similar to control the device via smartphones, computer, remote, to see the environmental situation and device battery and/or cartridge levels.

The present invention can be configured as a portable device used in an office, bedrooms, camping, living rooms, automobiles, airplanes, and any indoor or outdoor location. Optionally, the system is configured with a personal spray nozzle where one can spray oneself.

The microcomputer interface is programmable with the ability to program the device to work by time/environmental condition. The system and method of the present invention will assist in fixing SBS—Sick Building Syndrome, by reducing the amount of bad germs in the building space, and by that increasing vitality.

The system also has a sensor that checks not only the quality of germs in the air but also a sensor that senses the movement of air, so as soon as the HVAC system turns on, the device senses it and turns itself on according a dispense mist, this way there is no wasted solution material. This also disables access liquids to be in the HVAC while not working, which would cause more bacteria, enables a better usage of material.

In one embodiment, the invention is a system for dispersing a solution comprising:
a solution chamber having an inlet, an outlet, and a solution contained therein;

a venturi configuration operatively associated with said solution chamber;

an air inlet configured for imparting venturi effect on the solution in the solution chamber;

at least one actuator associated with a pressurized air inlet source; whereby, upon actuation, said pressurized air atomizes the solution and forces the atomized solution though the outlet.

In one embodiment, the solution contains at least one active material containing at least one of a medicament, probiotic, nutraceutical, or combinations thereof.

The venturi configuration includes air inlet and outlets to impart venturi effect on the solution.

The system actuator is a manually operated actuator, automated actuator controlled by a programmable computer microprocessor, or combinations thereof.

In one embodiment, the system has at least one sensor operatively associated with the actuator.

The system can be configured with at least one airflow sensor operatively associated with the actuator.

In one embodiment, the system has an outlet that directs atomized solution into an HVAC system into one of HVAC system inlet, HVAC system airflow duct, or combinations thereof.

The present invention also includes a method for delivering atomized solution, said method comprising the steps of:
providing a system as disclosed herein;
placing a solution in the solution chamber;
activating the actuator, whereby said activating atomizes the solution and said solution exits the solution chamber through the outlet.

The method includes solution in the chamber containing at least one active component. Active component include, but are not limited to a medicament, probiotic, Nutraceutical (whereby Nutraceutical includes, but is not limited to, vitamins, minerals, homeopathic materials/remedies and the like), or combinations thereof.

The method further includes the steps of measuring the interior volume of a room, calculating a desired final concentration of the atomized solution in said room and configuring the actuator to atomize for a calculated time period based on said desired final concentration. In one embodiment, the actuation is initiated based on interior environmental conditions.

In one embodiment, the method further comprises the step of measuring bacterial growth before and after delivery of the probiotic for a calculated time period based on said desired final concentration results in a bacterial growth measurement below about 100 fungal counts CT/cm2.

BRIEF DESCRIPTION OF THE SEVERAL VIEWS OF THE DRAWINGS

FIG. 16 is a chart with the data points from FIG. 15.

FIG. 18 is a chart with the data points from FIG. 17.

FIG. 20 is a chart with the data points from FIG. 19.

FIG. 22 is a chart with the data points from FIG. 21.

DETAILED DESCRIPTION OF THE PREFERRED EMBODIMENT

Figure 1:
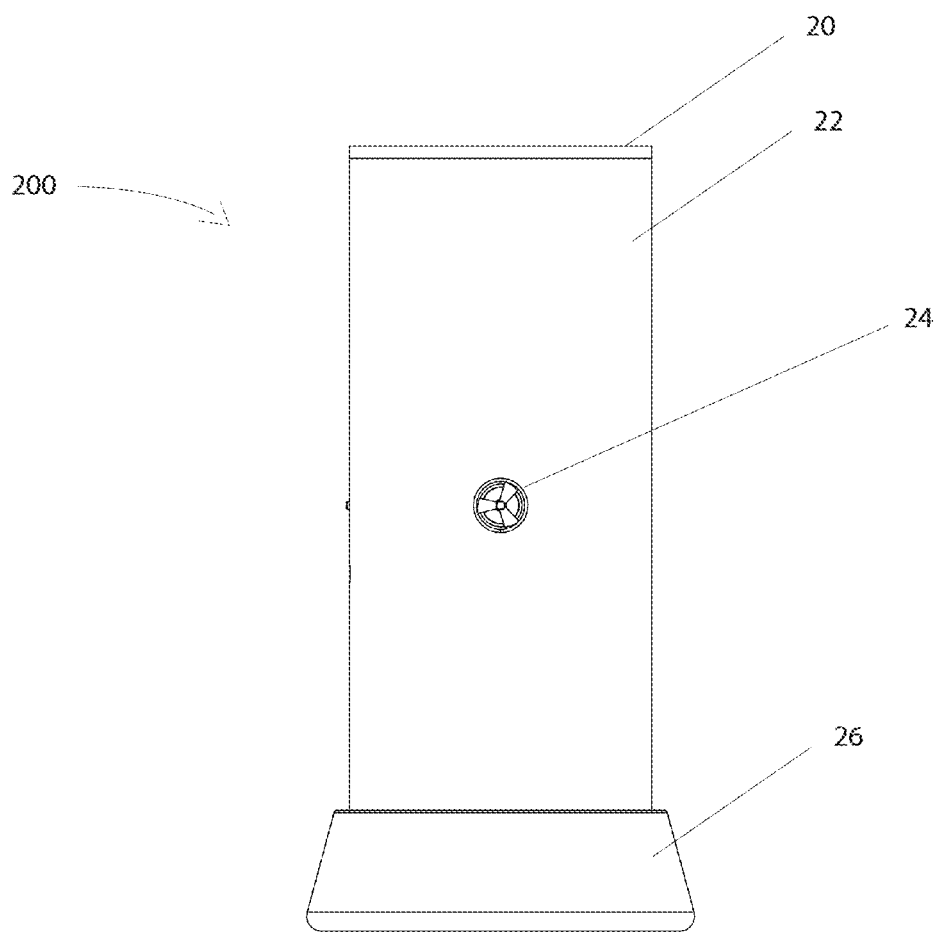
FIG. 1 is a front view of one embodiment of the dispersing apparatus of the present invention in the standing position.

Referring to the drawings, solution dispersing apparatus, as seen in FIG. 1, is configured atomize a solution having at least one active component and release the atomized solution into the air. The dispersing apparatus may be made, but not limited to, a variety of materials such as metals, plastics, woods, composites, glass, ceramics or combinations thereof.

As seen in FIG. 1 apparatus 200, in one configuration, will stand vertically on flat surfaces such as floors, counter tops or others, by placing it on base 26. As generally presented, apparatus 200 has liquid compartment cap 20 incorporated onto main body 22 having a solution outlet 24. In one embodiment, base 26 is configured to recharge a battery contained within main body 22.

Figure 2:
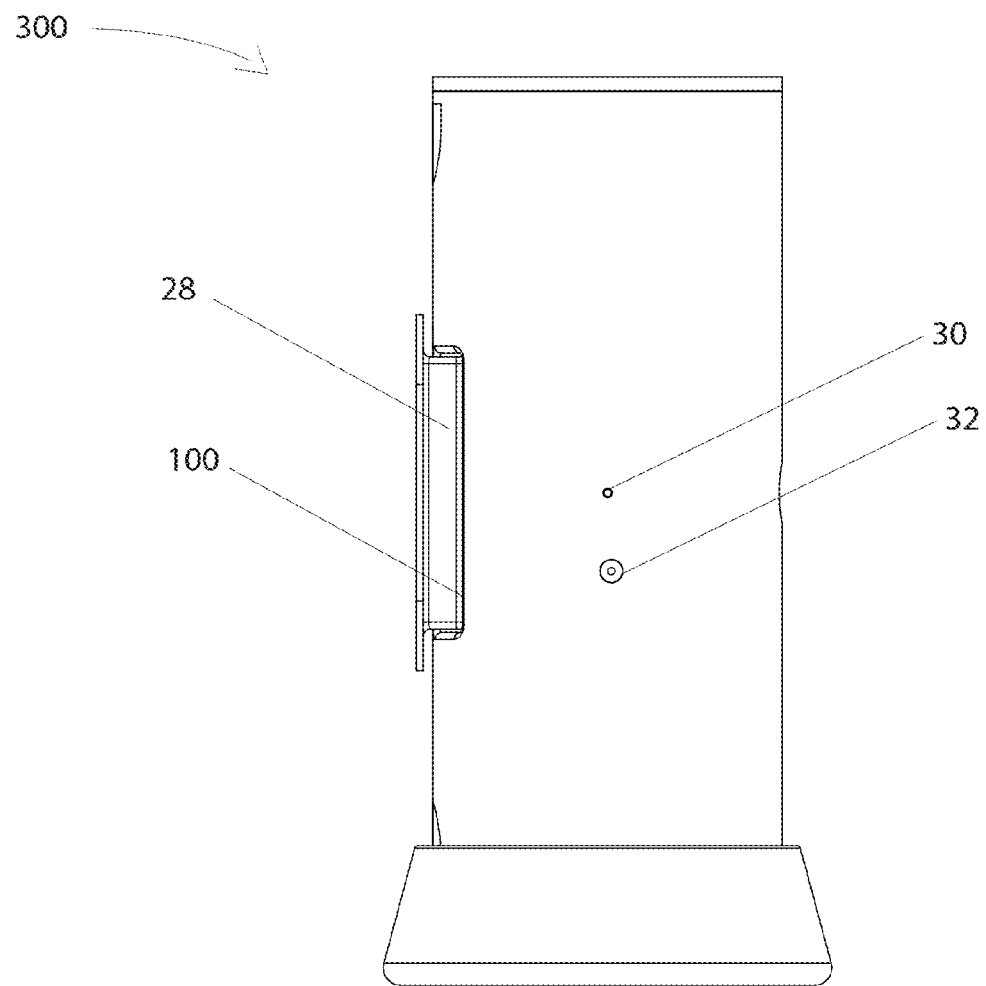
FIG. 2 is a side view of one embodiment of the dispersing apparatus of the present invention in the standing position thereof.

FIG. 2 is demonstrative of an embodiment in which apparatus 300 has horizontal wall mount 28 incorporated onto main body 22. The apparatus further includes an instant mist release button 30 and a data port or sensor cable socket 32. In this embodiment, apparatus 300 is configured for manual delivery of atomized solution as well as automated or computer controlled delivery via transmission of delivery commands to the actuator via port 32.

Figure 3:
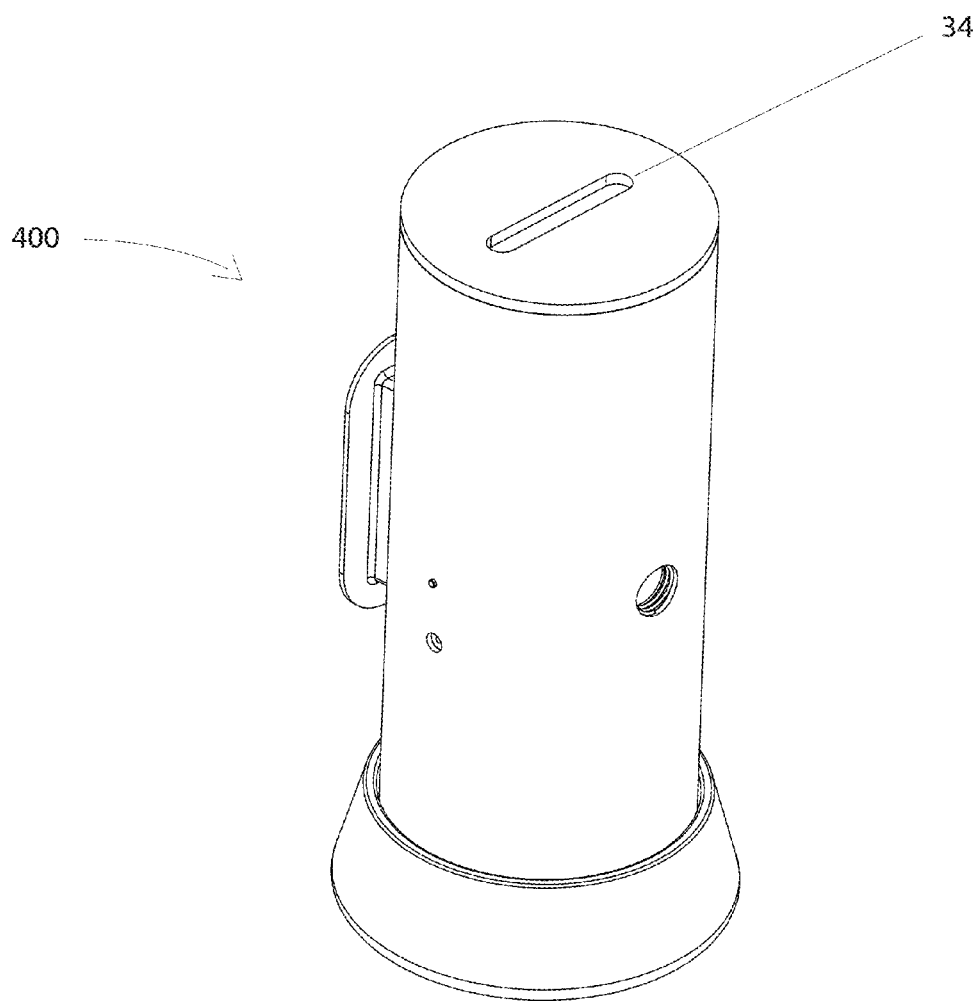
FIG. 3 is a perspective view of one embodiment of the dispersing apparatus of the present invention in the standing position thereof.
Figure 4:
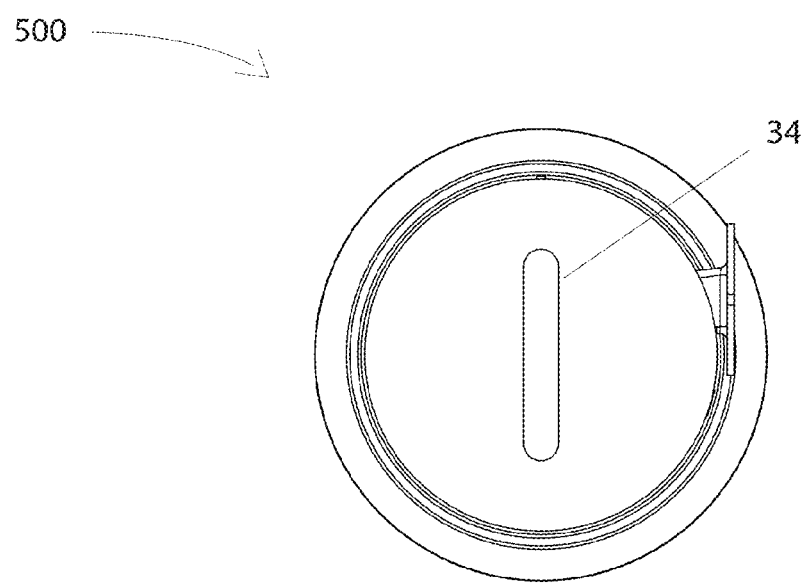
FIG. 4 is a top view of the dispersing apparatus of the present invention in the standing position thereof.

In one embodiment, as shown in FIGS. 3 and 4, solution container 400 has solution container window 34 incorporated thereon whereby a user is able to view liquid level of delivery solution contained within solution container 400.

Figure 5:
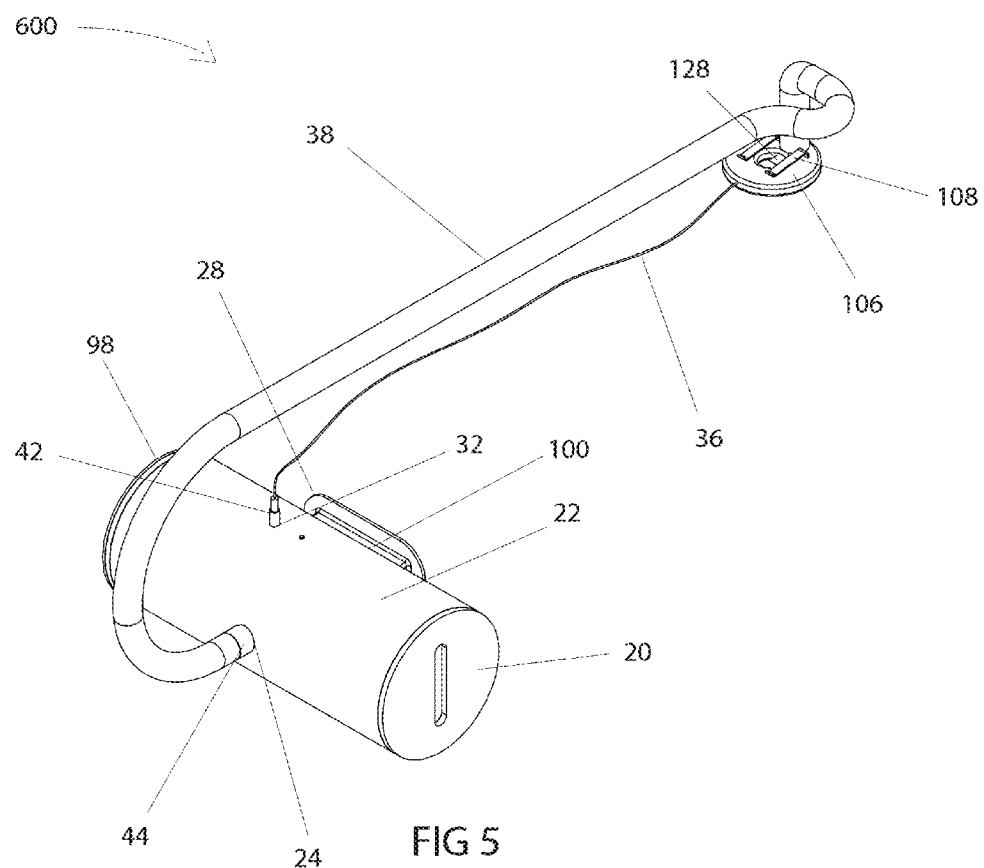
FIG. 5 is a perspective view of the dispersing apparatus of the present invention with air sensor accessory and hose.

As seen in FIG. 5, system 600 includes liquid compartment cap 20 incorporated onto main body 22 in which a solution outlet 24 is configured therewith. In one embodiment, horizontal wall mount 28 is included. System 600 further includes a data port or sensor cable socket 32 configured to receive sensor cable 36 with sensor cable connector 42. A solution hose 38 connected to outlet 24 at connector 44 directs atomized solution in a desired direction. Main body 22 is constructed to include an interior cavity cap in which components are housed.

In one embodiment, system 600 further includes at least one sensor 106 and sensor AC/HVAC clip 108.

In one embodiment a movable tab 128 is included. One nonlimiting example tab 128 as a nylon tab that moves when there is air flow so FIG. 6 movement sensor 54 sees the nylon moving, and could cause the device to turn on whenever AC is in operation.

Figure 6:
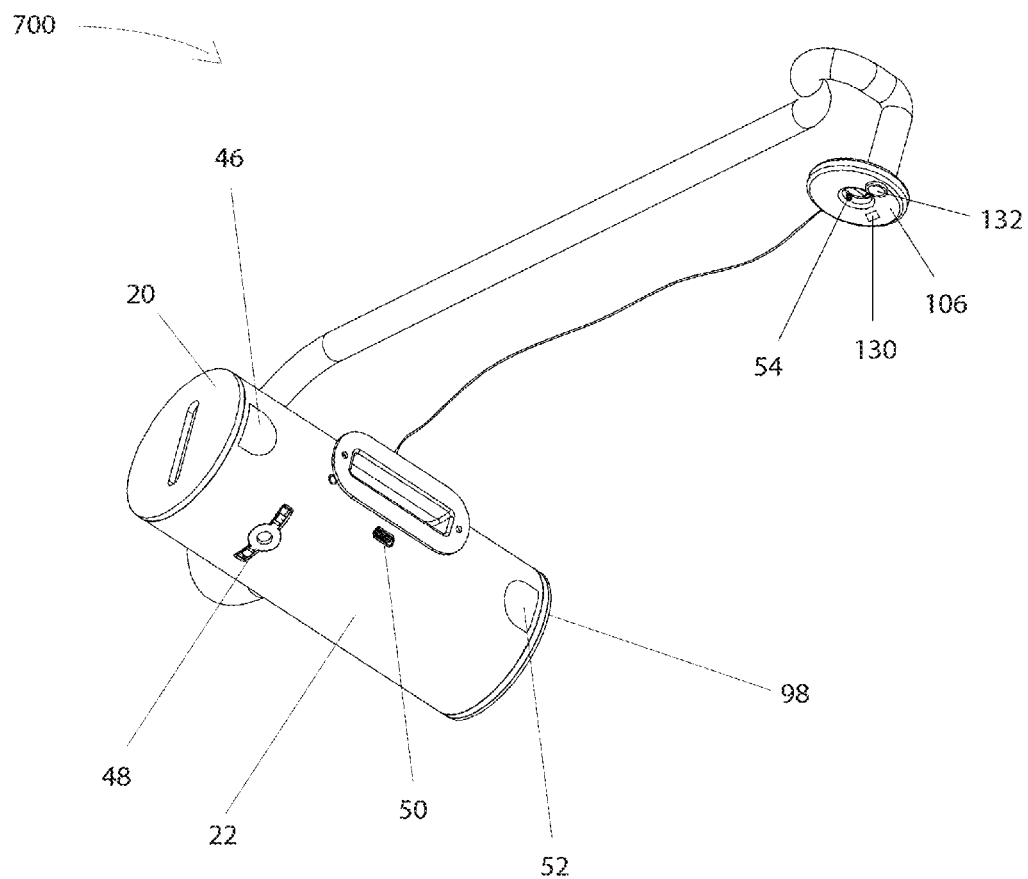
FIG. 6 is a perspective bottom view of the dispersing apparatus of the present invention with airflow sensor accessory and hose in the wall mounted position thereof.

In the embodiment demonstrated in FIG. 6, system 700 includes main body 22 having a first release button 46 for battery compartment air intake 48, a data connector 50, a second release button 52 for accessing the cavity holding solution chamber. Also present are movement sensor 54 operatively associated with movable tab 128 and chemical (Germs/Bacteria) sensor 106 and extension hose outlet 132. In one embodiment apparatus 700 includes ATP Sensor 130

Figure 7:
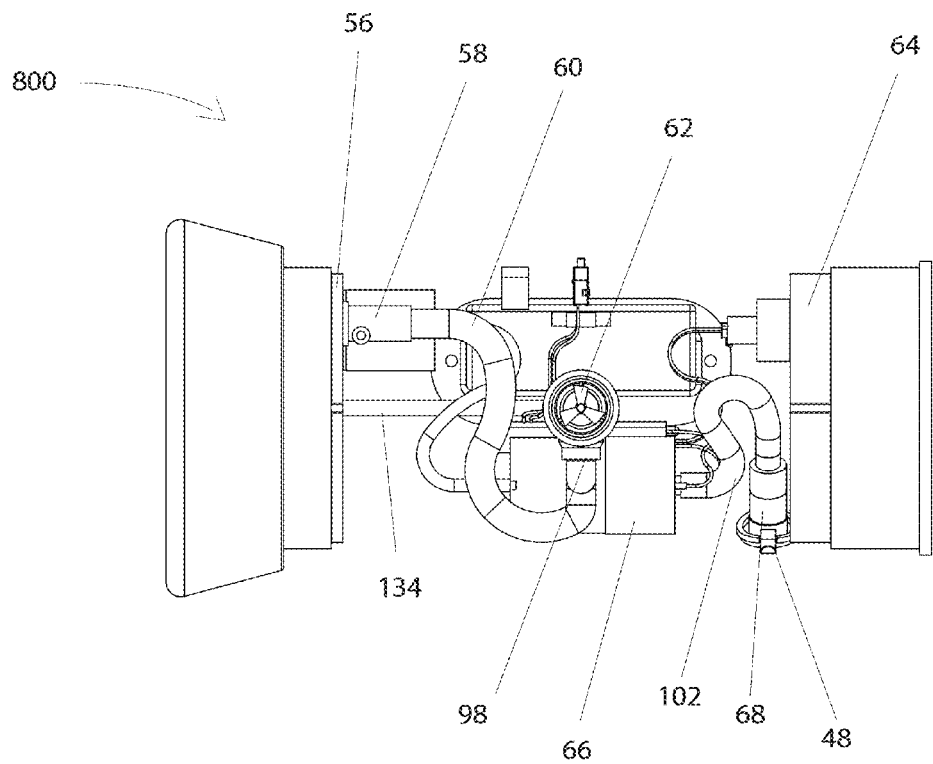
FIG. 7 is a front view of the dispersing apparatus of the present invention with main compartment removed in the wall-mounted position thereof.

In the configuration shown in FIG. 7, system 800 a liquid or solution chamber 56 has anti liquid stopper 58 associated therewith. Solution hose 60 is associated with fan 62 for moving atomized solution. The configuration further includes a battery compartment 64 and an air compressor 66 configured to receive inlet from air intake 68.

Figure 8:
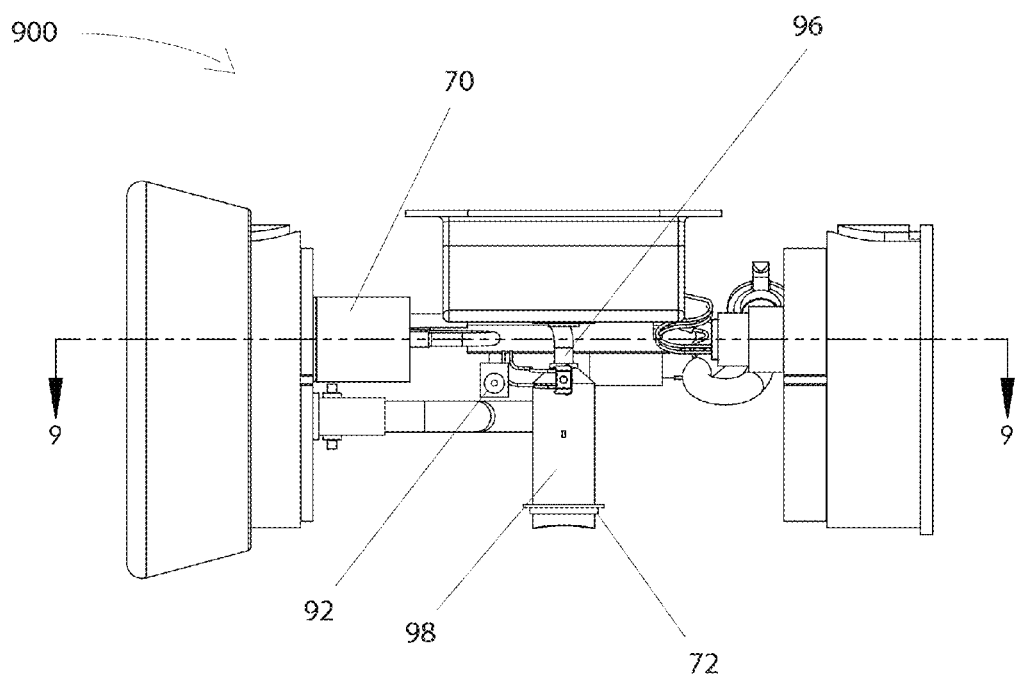
FIG. 8 is a side view of the dispersing apparatus of the present invention with main compartment removed in the wall-mounted position thereof.

In the configuration shown in FIG. 8 system 900 is configured with venturi chamber 70 operatively associated with internal sensor 92 and access liquids hose 96 whereby outlet hose extends from chamber cavity 98 that is sealed with chamber cavity 72.

Figure 9:
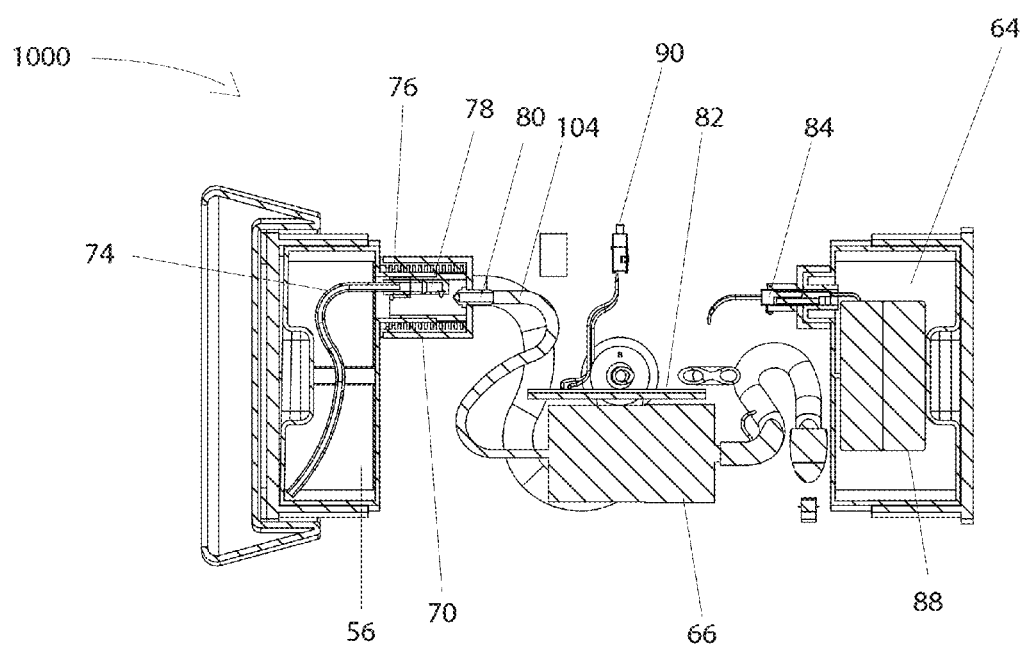
FIG. 9 is a front cut view of the dispersing apparatus of the present invention with compartment removed in the wall-mounted position thereof.

FIG. 9 is section view along lines 9-9 from FIG. 8 and demonstrates system 1000 having the varying connective components of the system. Battery compartment 64 houses battery 88 and connector cable 84 extends outward from compartment 64 and connect to circuit board 82. Air compressor 66 is controlled by circuit board 82 and further can be operated by manual actuator 90. Compressor outlet hose 104 is connected to Venturi chamber 70. Venturi chamber 70 has contained therein a reverse Venturi connector 76 and a reverse Venturi 78. Outlet hose 104 connects at Venturi 80 and reverse Venturi hose 74 connects solution chamber 56 with reverse Venturi 78.

Figure 10:
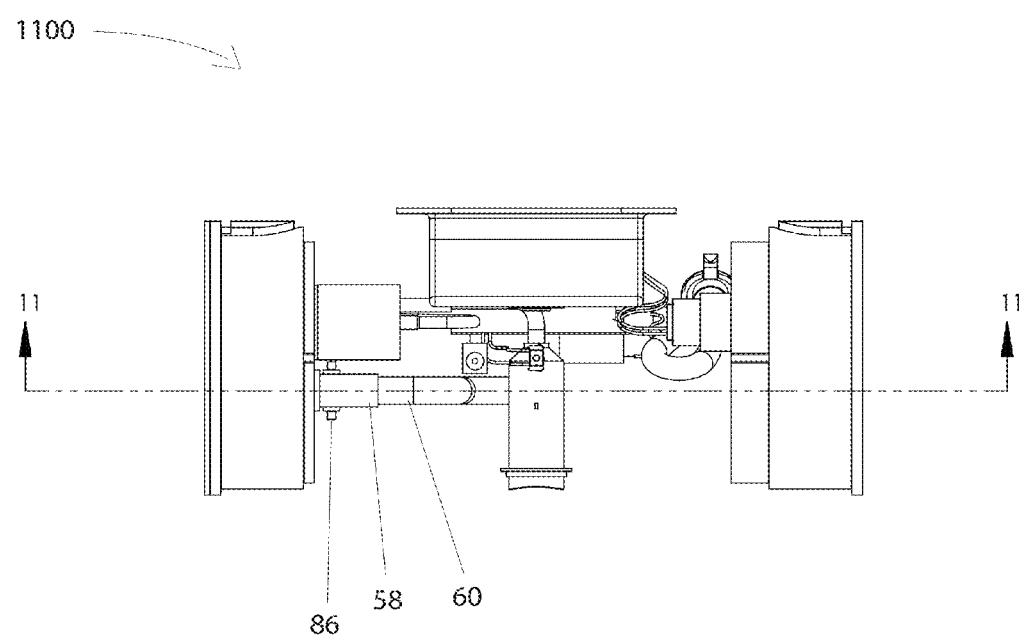
FIG. 10 is a side view of the dispersing apparatus of the present invention with main compartment removed in the wall-mounted position thereof.

FIG. 10 shows the outside of system configuration 1100 anti-liquid stopper valve 86 associated with and a liquid stopper 58 and outlet hose 60.

Figure 11:
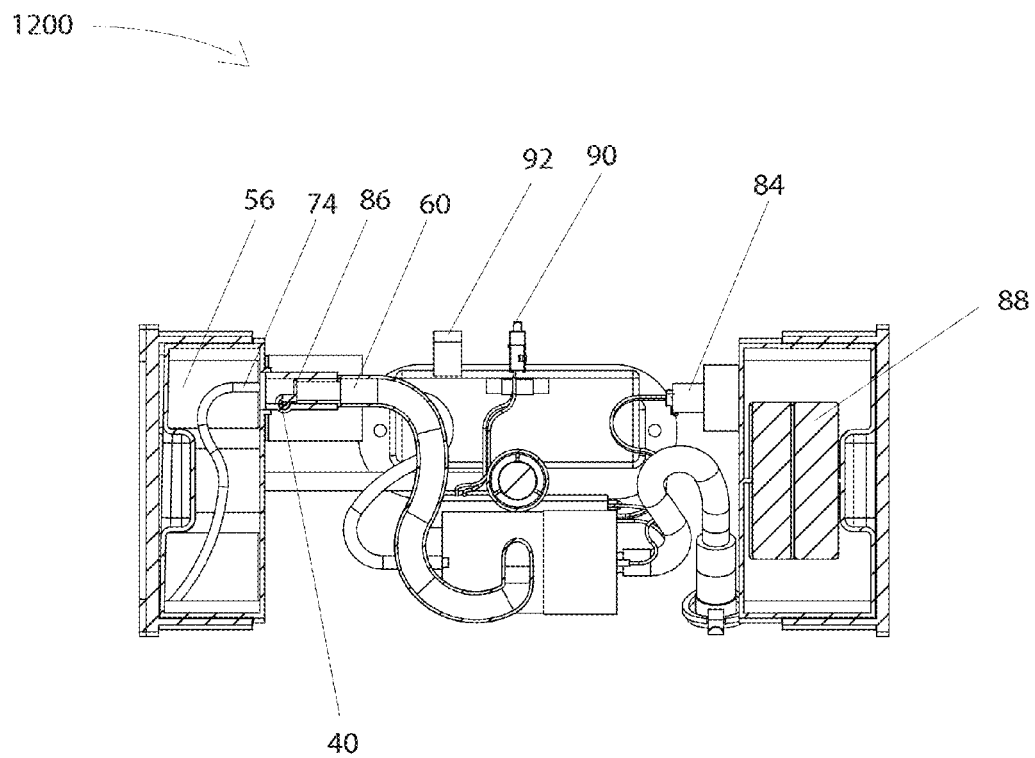
FIG. 11 is a front cut view of the dispersing apparatus of the present invention with main compartment and base removed in the wall-mounted position thereof.

FIG. 11 is a cross section along lines 11-11 from FIG. 10 whereby a configuration 1200 anti-spill hinge 40 configured with anti-liquid stopper valve 86 positioned between liquid chamber 56 and outlet hose 60.

Figure 12:
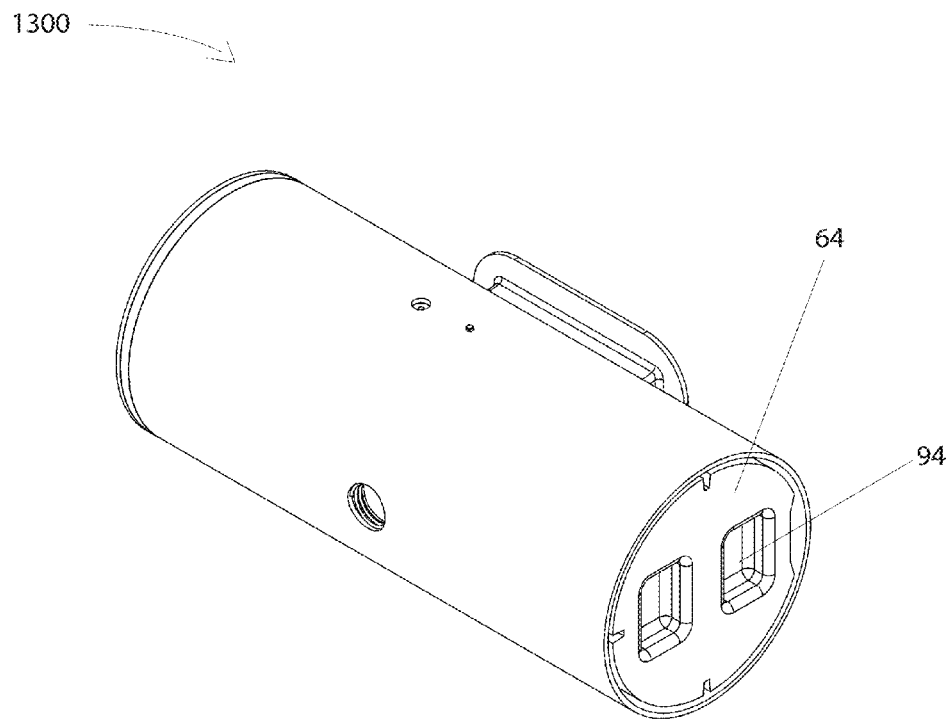
FIG. 12 is a perspective view of the dispersing apparatus of the present invention with one lid and base removed in the wall mounted position thereof.

FIG. 12 demonstrates a particular configuration 1300 whereby battery compartment 64 has finger grips 94 for grasping and removing cover.

Figure 13:
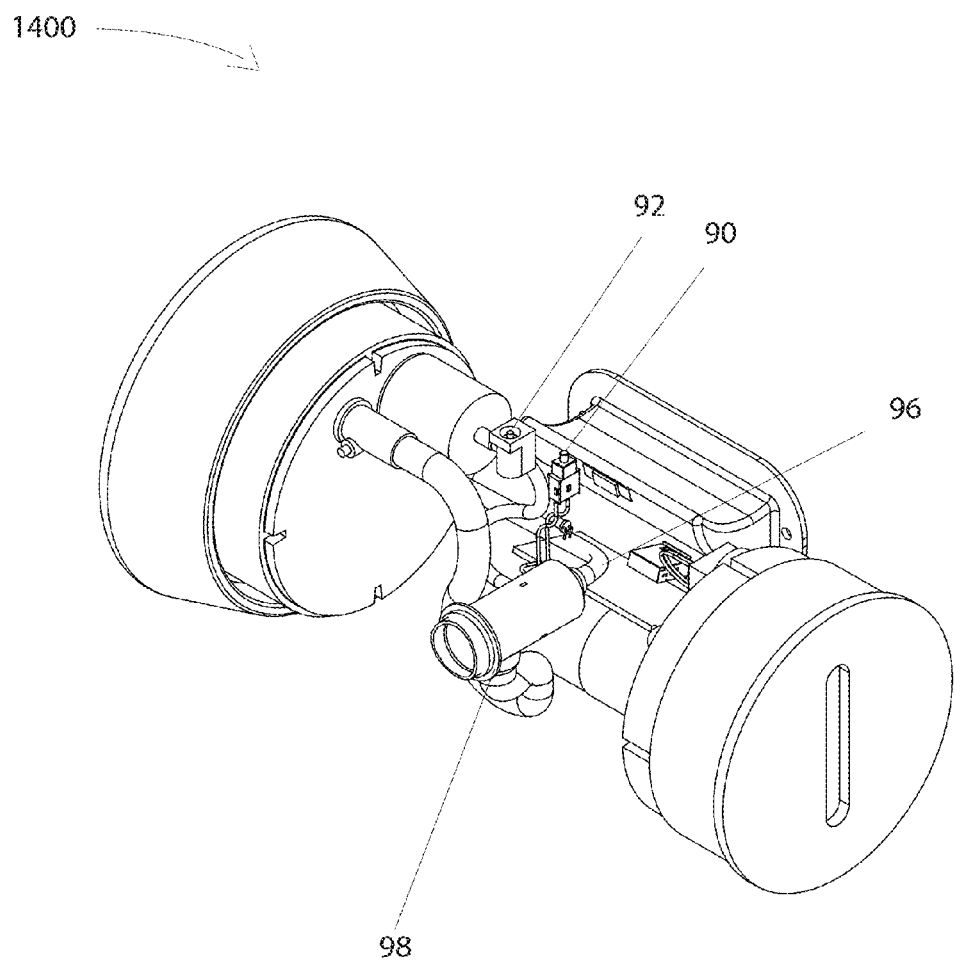
FIG. 13 is a perspective view of the dispersing apparatus of the present invention with main compartment removed in the wall-mounted position thereof.

FIG. 13 demonstrates a configuration 1400 whereby instant release actuator 90 and sensor connector 92 are positioned to actuate air to cavity 98. Although the particular figure demonstrates each of actuator 90 and sensor 92, it is contemplated that any particular configuration includes either one or both of these features. Alternatively, an embodiment is contemplated whereby the system and method does not include the biological, chemical, or airflow sensors.

Figure 14:
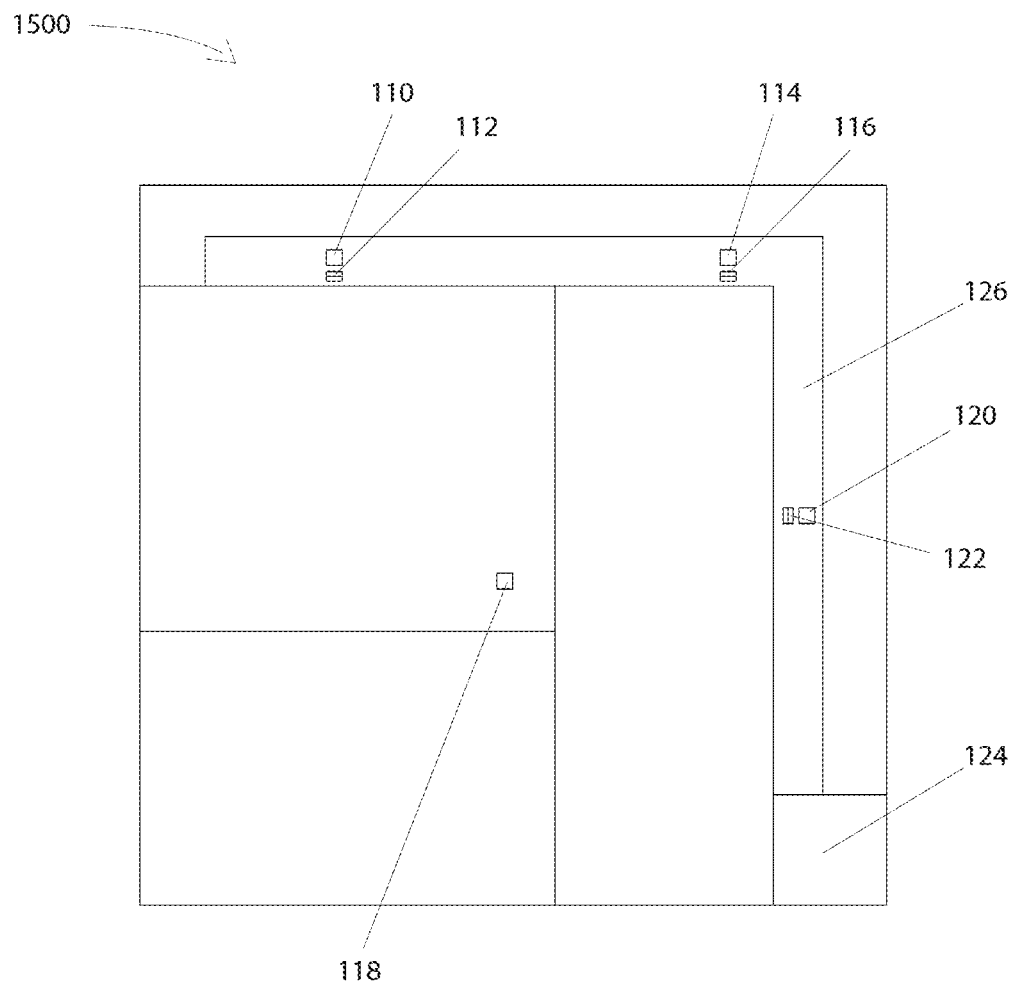
FIG. 14 is demonstrative of an interior floor plan of the present invention with sensors positioned in HVAC ductwork and interior rooms.

FIG. 14 is floor plan arrangement 1500 whereby sensors are positioned either within HVAC duct 126, or a room sensor 118 is positioned with in the interior volume of an indoor room. HVAC duct 126 is connected to AC or air handler 124. First sensor 110 is positioned in or near first AC air vent 112, second sensor 114 is positioned in or near second AC air vent 116, and third sensor 120 is positioned in or near second AC air vent 122. Although the particular figure demonstrates each of the sensors, it is contemplated that the number of sensors can be varied as desired in a particular configuration.

The system and method of the present invention is unique in that sensors are configured to actuate itemization of a delivery solution based upon particularized measurements.

In one nonlimiting example, the sensors are configured using the standard index of microbial air contamination (IMA). As is known in the art, the standard index of microbial air contamination (IMA) for the measurement of microbial air contamination in environments at risk is described. The method quantifies the microbial flow directly related to the contamination of surfaces coming from microbes that reach critical points by falling on to them. The index of microbial air contamination is based on the count of the microbial fallout on to Petri dishes left open to the air according to the 1/1/1 scheme (for 1 h, 1 m from the floor, at least 1 m away from walls or any obstacle). Classes of contamination and maximum acceptable levels have been established. The index of microbial air contamination has been tested in many different places: in hospitals, in food industries, in art galleries, aboard the MIR space station and also in the open air. It has proved to be a reliable and useful tool for monitoring the microbial surface contamination settling from the air in any environment.

In order to combat microbial growth, an anti-microbial probiotic solution is used in the system and method of the present invention. As will be set forth below, laboratory testing has demonstrated the delivery of atomized probiotic using the system and method of the present invention has been proven to reduce live microbial species.

The Sensor may cause the system to turn on/off according to the environmental condition result.

The actuator initiates air into the solution container, and the solution is atomized by a venturi effect and exits the solution chamber. The atomized solution is then directed as desired from the assembly Testing and Results The system and method of the present invention was tested using Probiotic solution as the atomizing solution.

Initial swab tests were performed prior to delivering the atomized probiotic solution. The areas inside the test area were sampled and analyzed for existence of fungal contaminants (QT and QL), by an accredited and certified environmental microbiology laboratory.

After initial swabbing, following Probiotic treatment via a the unique aerosolization system and method of the present invention which distributes a measured amount of the Bio-Zone Probiotic mixture on infected areas at a predetermined schedule according to needs.

Fungal samples were collected and sent to an analytical, mycology LAB in the USA.

a) Creating an "in vitro" environment in accordance with ISO 13697; 2001 criteria.

b) Collection Media: agar samples—OGYE+oxytetracycline Hydrochloride (@) 10 cm2 c) A Patented probiotic Mixture of *Bacillus* spp. (BioZone Probiotic®) which includes: *Bacillus coagulans, Bacillus lentus, Bacillus lichenijormis,* and *Bacillus pumilus*. All Grade One safety level according to the FDA.
d) Mikropor filter F8, Dimension: 592/592/292 mm
e) Intervals of Sampling/elapsed time:
Control (0)
24 Hours
48 Hours
72 Hours
f) The collected samples were packed and shipped according to the environmental laboratory requirements.

Results

Collection of samples from the main filters of an AHU (Air Handling Unit) and analyzed the results at a certified accredited and registered environmental microbiology LAB.

Summary

The results we obtained by using BioZone Probiotics/EBA on two main filters of AHU were excellent and encouraging.

Figure 15:
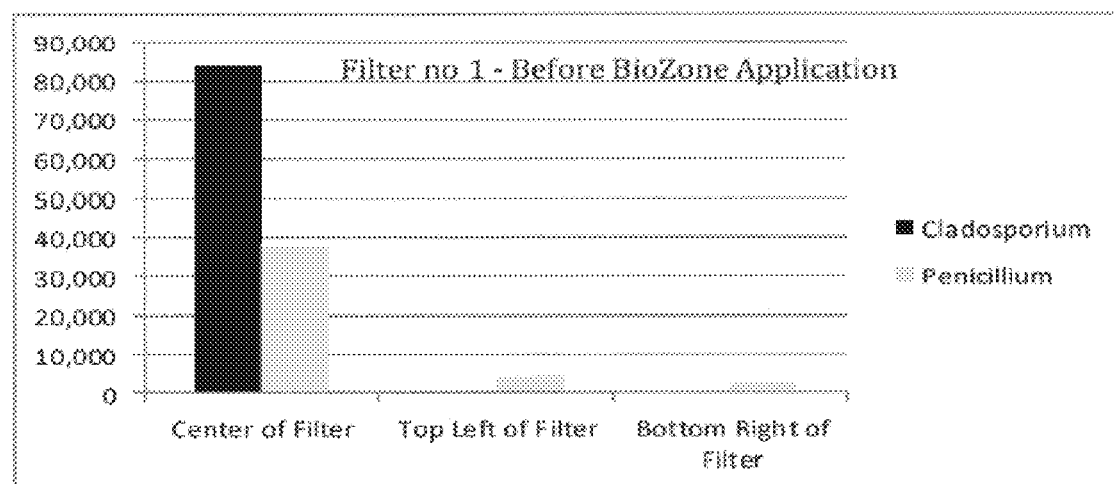
FIG. 15 is a graph demonstrating biological measurements before the system and method of the present invention are used.

As demonstrated in FIGS. 15-22:

FIGS. 15 and 16 demonstrate quantified amounts of cladosporium and penicillium before use in the order of approx. 38,000 to 84,000 fungal counts in CT/cm2.

Figure 17:
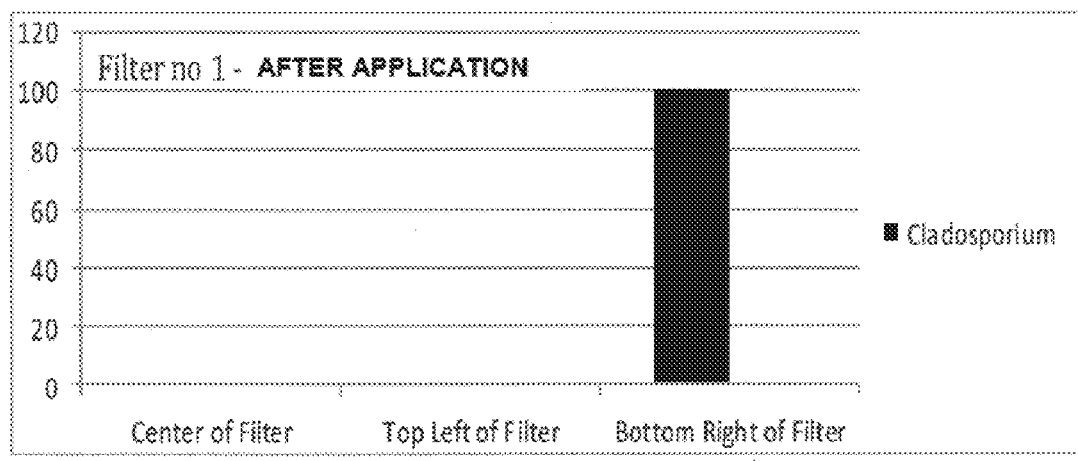
FIG. 17 is a graph demonstrating biological measurements after the system and method of the present invention are used.

FIGS. 17 and 18 demonstrate after using an atomized probiotic delivered with the system and method of the present invention, the measurements dropped to NFD (no fungi detected) in 2 locations and 100 count/cm2 in the bottom right of the tested filter.

Figure 19:
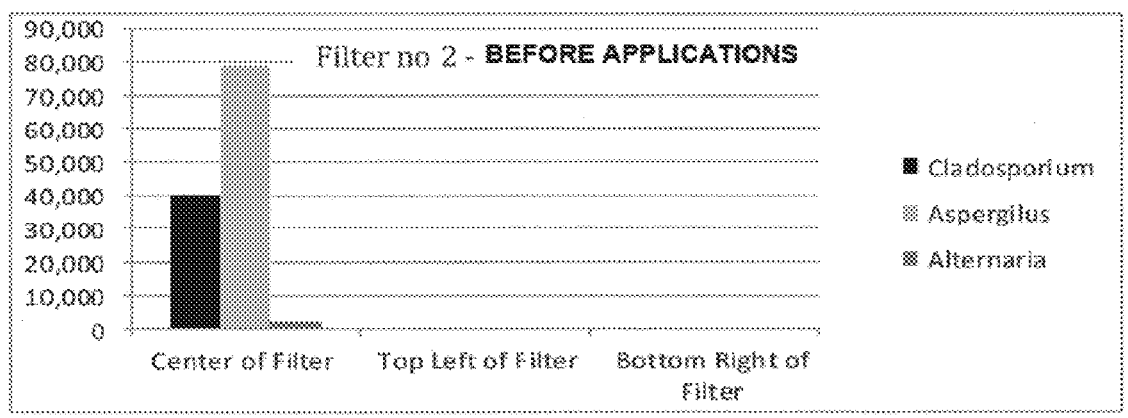
FIG. 19 is a graph demonstrating biological measurements on filter number 2 before the system and method of the present invention are used.

FIGS. 19 and 20 demonstrate quantified amounts of cladosporium, alternaria, and aspergilus, before use in the order of approx. 40,000, 2,000, and 78,000 fungal counts in CT/cm2.

Figure 21:
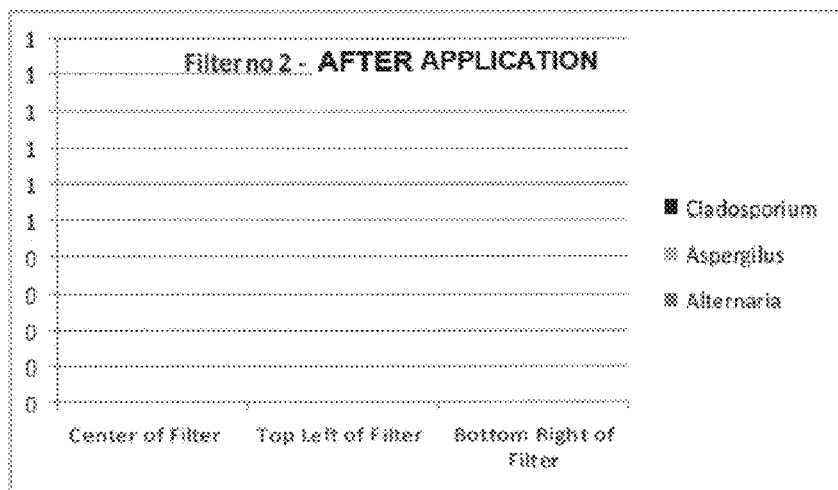
FIG. 21 is a graph demonstrating biological measurements on filter number 2 after the system and method of the present invention are used.

FIGS. 21 and 22 demonstrate after using an atomized probiotic delivered with the system and method of the present invention, the measurements dropped to NFD (no fungi detected).

The results confirm suitability of the system and method of the present invention for the use of environmental Probiotics for an efficient control of microbial (Bacterial/Fungal) growth.

The results further indicate that the system and method of the present invention would be suitable on a variety of objects such as fomites, textiles, construction materials and a variety of porous and semi-porous materials, and similar to those in hospitals, under similar environmental conditions such as; air temperature and relative humidity (40%-50% relative humidity and 1 Soc-22° C. Air temperature)

It is further contemplated that the present invention be configured to program the unit at initialization based on size of space (cubic volume) and initial level of contamination (where known or estimated).

Additionally, if future technology advances to provide real-time testing of microbial activity, the present invention is suitable for use with such testing.

Additionally, the present invention is unique in that the mechanical process of solution atomization uses the Venturi effect.

The present invention requires care with the 2 venturi channels in order to make it working as you have to have 2 narrow channels or pipes into a container one to push air in and one to have the liquid broken to tiny droplets (atomization).

Currently, since the venturi components must be very narrow in diameter, providing a replacement cartridge is cumbersome as one needs to unscrew a cap and carefully take the whole nebulizer without breaking or bending and place a new one.

The present invention configures the system for easily replacing a sophisticated cartridge that has this mechanism built in every cartridge that make it easier for replacement.

The solution cartridge has the nebulizer siting in a cap holder of the cartridge—a fixed part that never to be replaced.

The "connection" is achieved by very accurate mechanism that ensure that the sliding cartridge meets its matching pipe by touching which requires accuracy to level of more than $\frac{1}{10}$ mm The present invention is a mechanical improvement of the Venturi system for the consumer market, indirectly creating very inexpensive cartridges It is further contemplated that the system and method of the present invention be used for the wide administration of an inhaled medicament, for example, a hospital has an outbreak of a bacterial infection, and an antibiotic can be atomized and distributed throughout the entire building.

As previously discussed, the method of delivering solution according to the present invention requires consideration of solution concentration, air volume of the room or rooms effected, and desired final concentration of atomized solution.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A system for dispersing a solution comprising:
a solution chamber having an inlet, an outlet, and a solution contained therein;
a venturi configuration operatively associated with said solution chamber;
an air inlet associated with a pressurized air inlet source configured for imparting venturi effect on the solution in the solution chamber;
at least one actuator associated with a said pressurized air inlet source; and at least one sensor operatively associated with said at least one actuator, whereby, upon actuation, pressurized air from said pressurized air atomizes the solution and forces the atomized solution though the outlet.

2. The system of claim 1 wherein the solution contains at least one active material.

3. The system of claim 1 wherein the solution in the chamber contains at least one of a medicament, probiotic, nutraceutical, or combinations thereof.

4. The system of claim 1 wherein said venturi configuration includes air inlet and outlets to impart venturi effect on the solution.

5. The system of claim 1 wherein the actuator is a manually operated actuator.

6. The system of claim 1 wherein the actuator is an automated actuator controlled by a computer microprocessor.

7. The system of claim 1 further comprising at least one airflow, chemical, biological sensor, or combinations thereof operatively associated with the actuator.

8. The system of claim 1 having an outlet that directs atomized solution into an HVAC system.

9. The system of claim 1 having an outlet that directs atomized solution into an HVAC system inlet.

10. The system of claim 1 having an outlet that directs atomized solution into an HVAC system airflow duct.

11. A method for delivering atomized solution, said method comprising the steps of:

providing a system for dispersing a solution comprising:

a solution chamber having an inlet, an outlet, and a solution contained therein;

a venturi configuration operatively associated with said solution chamber;

an air inlet associated with a pressurized air inlet source configured for imparting venturi effect on the solution in the solution chamber;

at least one actuator associated with a said pressurized air inlet source; and at least one sensor operatively associated with said at least one actuator, whereby, upon actuation, pressurized air from said pressurized air atomizes the solution and forces the atomized solution though the outlet;

placing a solution in the solution chamber;

measuring bacterial growth, either before or after delivery of the solution, and calculating a time period of delivery based on said desired final concentration results in a bacterial growth measurement below about 100 fungal counts $CT/cm2$;

activating the actuator, whereby said activating atomizes the solution and said solution exits the solution chamber through the outlet.

12. The method of claim 11 wherein said solution in the chamber contains at least one of a medicament, probiotic, nutraceutical, or combinations thereof.

13. The method of claim 11 further including the steps of measuring the interior volume of a room, calculating a desired final concentration of the atomized solution in said room and configuring the actuator to atomize for a calculated time period based on said desired final concentration.

14. The method of claim 11 whereby said solution is a probiotic medicament, nutraceutical, or combinations thereof.

* * * * *